United States Patent [19]

Keller

[11] Plant 5,236

[45] May 22, 1984

[54] DISTINCT VARIETY OF STREPTOCARPUS NAMED VRENI

[75] Inventor: Emil Keller, Hedingen, Switzerland

[73] Assignee: Oglevee Associates, Inc., Connellsville, Pa.

[21] Appl. No.: 452,820

[22] Filed: Dec. 28, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

The new cultivar is generally characterized by a two-tone coloration, rose pink to purple, with a distinct veining. It is further characterized by small flowers and a compact and short plant.

1 Drawing Figure

BACKGROUND OF THE NEW PLANT

The present invention comprises a new and distinct cultivar of *Streptocarpus* × *hybridus* known by the varietal name Vreni. The new cultivar was developed in a breeding program and is a cross of the varieties Kolibir III (pollen parent) and Tina (seed parent). The new cultivar is distinguished from its parentage by its shorter leaves, early blooming and darker flower color. It is similar to its parentage in respect of its shape and design of the flowers and leaves.

The new cultivar is characterized by a two-tone coloration, rose pink to purple, with a distinct veining. It is further characterized by small flowers and a compact and short plant.

The new cultivar was discovered in 1979 in Hedingen, Switzerland; was first asexually reproduced by cuttings in Hedingen, Switzerland; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa. has a response time of nine weeks. This response time is measured from a plantlet which is a well rooted young plant in a five centimeter pot to a flowering plant in a fifteen centimeter pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by the Oglevee Floral Company in Connellsville, Pa. The plant history was taken on nine week plants blossomed under natural light in a greenhouse and color readings were also taken using natural sunlight. Color references are primarily to the R.H.S. color chart of The Royal Horticultural Society of London. Some color reference is to Exotica III and such reference is duly noted.

Botanical classification: Gesneriaceae (family); *Streptocarpus* × *hybridus* (genus × species).

Flower:

*Fully expanded.*—3 to 4.5 centimeters.

*Borne.*—In clusters of four to eight flowers per flower stalk. Flower stalks arise close together and initiate at base of leaf.

*Stems.*—Single, round and pubescent.

*Form.*—Funnel formed in an umbel.

*Permanence.*—Long lasting 21 to 25 days.

Color:

*Tonality from a distance.*—Two-tone rose pink to purple (Exotica III) with distinct veining.

*Front of petals.*—Background Fan 2 Red Purple Group 68-B. Toning Fan 2 Red Purple Group 64-A.

*Base of petals.*—Fan 2 Red Purple Group 65-C.

*Throat.*—Veining Fan 2 Red Purple Group 71-A.

*Reverse of petals.*—Fan 2 Purple Group 75-C.

*Discoloration.*—Insignificant.

Petals:

*Texture.*—Velvet.

*Appearance.*—Individually lobed and slightly cuneate margin.

*Arrangement.*—Regularly united into elliptical form.

*Persistence.*—21 to 25 days and remains on plant in dry form until picked.

*Fragrance.*—None.

Reproductive organs:

*Anthers.*—Four per flower, two perfectly formed stamens which are attached and two imperfectly formed stamens which are unattached.

*Filament.*—The perfectly formed are 1.5 centimeters up from the base and 0.5 centimeter long. The imperfectly formed initiate 1.5 centimeters up from the base and are 1 to 3 millimeters long.

*Pollen.*—Generally nonfertile.

*Style.*—Plain white 0.6 centimeter long ending in a flattened stigma tinted purple.

*Ovaries.*—Include purple streaks and are long and narrow being 1.1 to 1.3 centimeters long and 2 to 3 millimeters in diameter.

Plant:

*Form.*—Leaves rosette from a crown at the soil line.

*Growth.*—A spreading, free flowing habit.

*Height from soil line.*—12 to 15 centimeters.

*Spread.*—27 to 35 centimeters.

Foliage:

*Top side.*—Fan 3 Green Group 137-B.
*Under side.*—Fan 4 Greyed Green Group 193-A.
*Size.*—12 to 28 centimeters long and 4.5 to 7 centimers wide at the widest point.
*Quantity.*—5 to 8 leaves.
*Shape.*—Linear.
*Ribs and veins.*—Pinnate.
*Rib and vein color.*—Fan 3 Green Group 138-B.

*Margin.*—Cuneate.
*Leaf tip.*—Obtuse, with some acute.
*Leaf base.*—Attenuate.

I claim:

1. A new and distinct variety of Streptocarpus substantially as herein shown and described.

* * * * *

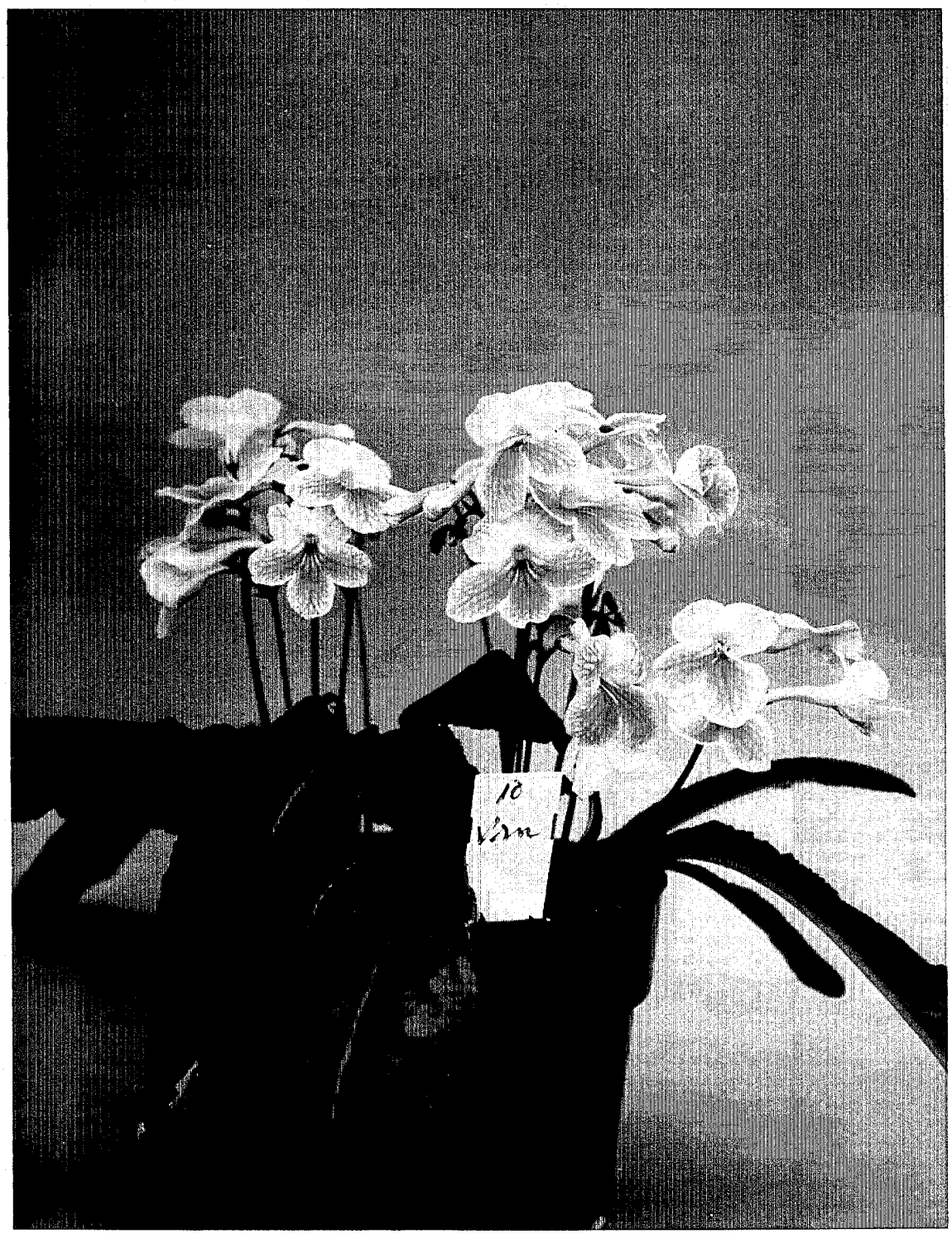
10
Van